United States Patent
Sreenivasan et al.

(10) Patent No.: US 11,616,740 B2
(45) Date of Patent: Mar. 28, 2023

(54) INVOKING CHATBOT IN ONLINE COMMUNICATION SESSION

(71) Applicant: KONINKLIJKE PHILIPS N.V., Eindhoven (NL)

(72) Inventors: Rithesh Sreenivasan, Bangalore (IN); Zoran Stankovic, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/276,383

(22) PCT Filed: Sep. 10, 2019

(86) PCT No.: PCT/EP2019/074034
§ 371 (c)(1),
(2) Date: Mar. 15, 2021

(87) PCT Pub. No.: WO2020/053172
PCT Pub. Date: Mar. 19, 2020

(65) Prior Publication Data
US 2022/0078139 A1    Mar. 10, 2022

(30) Foreign Application Priority Data
Sep. 14, 2018 (EP) .................................... 18194568

(51) Int. Cl.
*H04L 51/02* (2022.01)
*G16H 80/00* (2018.01)
*G10L 15/18* (2013.01)

(52) U.S. Cl.
CPC .............. *H04L 51/02* (2013.01); *G10L 15/18* (2013.01); *G16H 80/00* (2018.01)

(58) Field of Classification Search
CPC .......... H04L 51/02; G16H 80/00; G10L 15/18
USPC ........................................................ 709/206
See application file for complete search history.

(56) References Cited

U.S. PATENT DOCUMENTS

| | | | |
|---|---|---|---|
| 9,504,021 B1 * | 11/2016 | Wurtenberger | ... H04W 28/0268 |
| 9,514,227 B1 | 12/2016 | Garrett et al. | |
| 9,761,222 B1 | 9/2017 | Scarasso et al. | |
| 10,270,864 B2 * | 4/2019 | Sagar | ..................... H04L 67/148 |

(Continued)

OTHER PUBLICATIONS

International Search Report and Written Opinion for International Application No. PCT/EP2019/074034, filed Sep. 10, 2019, 4 pages.
(Continued)

*Primary Examiner* — Tauqir Hussain (57) ABSTRACT

A chatbot may be invoked in an online communication session between two or more human users to share additional content in the communication session. To determine when to invoke the chatbot, e.g., at which point during their conversation, an interaction model may be trained on past conversation data between participants to determine so-termed interaction points in the past conversation data which are predictive of a subsequent sharing of additional content by one of the participants. Having generated the interaction model, the interaction model may be applied to an online communication session to detect such interaction points in a real-time or near real-time conversation between users and to invoke the chatbot to participate in the communication session in response to a detection.

14 Claims, 7 Drawing Sheets

(56) References Cited

U.S. PATENT DOCUMENTS

| | | | | |
|---|---|---|---|---|
| 10,491,547 | B2* | 11/2019 | Sagar | H04L 51/04 |
| 10,498,674 | B2* | 12/2019 | Sagar | H04L 67/1001 |
| 10,616,147 | B2* | 4/2020 | Viswanathan | G06F 16/273 |
| 10,698,745 | B2* | 6/2020 | Sturtivant | G06F 9/44526 |
| 10,951,552 | B2* | 3/2021 | Jafar Ali | G06F 40/295 |
| 10,965,623 | B2* | 3/2021 | Robbins | H04L 51/02 |
| 10,984,901 | B1* | 4/2021 | Locklear | G07F 11/52 |
| 11,050,684 | B2* | 6/2021 | Jernström | H04L 67/141 |
| 11,138,388 | B2* | 10/2021 | Emery | G06F 16/3329 |
| 11,140,101 | B2* | 10/2021 | Robbins | H04W 4/08 |
| 2004/0021765 | A1* | 2/2004 | Kubala | H04N 7/15 |
| | | | | 348/14.08 |
| 2007/0226295 | A1* | 9/2007 | Haruna | G06F 16/38 |
| | | | | 709/204 |
| 2010/0049817 | A1* | 2/2010 | Xu | H04L 51/56 |
| | | | | 709/206 |
| 2013/0003579 | A1* | 1/2013 | Lu | H04N 21/6405 |
| | | | | 370/252 |
| 2014/0133294 | A1* | 5/2014 | Horn | H04W 48/06 |
| | | | | 455/436 |
| 2016/0094490 | A1* | 3/2016 | Li | H04L 12/1813 |
| | | | | 709/206 |
| 2016/0134752 | A1* | 5/2016 | Aldecoa | H04M 3/2236 |
| | | | | 379/88.01 |
| 2016/0147971 | A1* | 5/2016 | Kolowitz | G06F 3/0482 |
| | | | | 715/753 |
| 2016/0158011 | A1* | 6/2016 | de Canniere | A61F 2/2463 |
| | | | | 623/2.37 |
| 2016/0352656 | A1 | 12/2016 | Galley et al. | |
| 2017/0039274 | A1* | 2/2017 | Kaleta | G06F 16/33 |
| 2017/0249710 | A1* | 8/2017 | Guillama | G06Q 10/00 |
| 2017/0345215 | A1* | 11/2017 | Khedkar | G06F 3/011 |
| 2018/0027444 | A1* | 1/2018 | Maria | H04W 28/0289 |
| | | | | 370/235 |
| 2018/0268318 | A1* | 9/2018 | Matam | G06F 40/216 |
| 2019/0037036 | A1* | 1/2019 | Sunkara | H04L 67/535 |
| 2019/0156222 | A1* | 5/2019 | Emma | G06N 5/041 |
| 2019/0215729 | A1* | 7/2019 | Oyman | H04L 65/1016 |
| 2019/0388787 | A1* | 12/2019 | Padmanabhan | G09B 19/00 |
| 2020/0143288 | A1* | 5/2020 | Eisenzopf | G06F 40/30 |
| 2020/0236068 | A1* | 7/2020 | TeNyenhuis | G06F 40/35 |
| 2020/0329088 | A1* | 10/2020 | Oyman | H04L 65/1016 |
| 2021/0006614 | A1* | 1/2021 | Oyman | H04L 65/70 |
| 2021/0027888 | A1* | 1/2021 | Singh Bhatia | G16H 40/20 |
| 2021/0144765 | A1* | 5/2021 | Edström | H04W 74/0816 |
| 2021/0157990 | A1* | 5/2021 | Lima | H04L 51/02 |
| 2021/0233627 | A1* | 7/2021 | Foley | G16H 50/20 |
| 2021/0330189 | A1* | 10/2021 | Rose | G16H 15/00 |

OTHER PUBLICATIONS

Serban, et al., "A Deep Reinforcement Learning Chatbot", Computer Science, Mathematics, Published 2017, pp. 1-40.

\* cited by examiner

INVOKING CHATBOT IN ONLINE COMMUNICATION SESSION

RELATED APPLICATIONS

This application is the U.S. National Phase application under 35 U.S.C. § 371 of International Application No. PCT/EP2019/074034, filed on Sep. 10, 2019, which claims the benefit and priority to European Application No. 18194568.4, filed Sep. 14, 2018, which is incorporated by reference in its entirety.

FIELD OF THE INVENTION

The invention relates to a system and a computer-implemented method for invoking a chatbot in an online communication session involving at least two participants, such as a medical professional and a patient.

The invention further relates to a server and client device comprising the system, and to a computer-readable medium comprising instructions for causing a processor system to perform the computer-implemented method.

BACKGROUND OF THE INVENTION

It is expected that communication between medical professionals such as clinicians or nurses and their patients is increasingly carried out online, for example to avoid the need for a patient to come to the hospital, or to facilitate access of patients within a hospital to a clinician or nurse. Here, the term 'online' may refer to the communication being carried out in a digital form using a communication network such as the Internet. Other examples of such communication networks include local area networks such as an internal network of a health care provider.

For example, such online communication may involve users using a client device to log onto or connect to a real-time or near real-time communication platform and to communicate via the communication platform via verbal and sometimes also non-verbal communication. Such communication may involve various communication modalities, such as text, audio (voice), video, etc., and typically takes place in communication sessions which may be referred to by their respective modality, e.g., an instant messaging session, a video conference, etc.

For example, medical professionals may communicate with their patients using video conferences. During these video conferences, the medical professional may wish to explain a clinical concept to a patient for a better engagement of the patient. Currently, the medical professional may either verbally explain the clinical concept or may share additional content such as a web-page or a video during the video conference to support the verbal explanation or render the verbal explanation unnecessary. Such sharing of additional content is supported by many communication platforms, and may involve a user sharing the additional content via a separate sharing mechanism provided by the communication platform, such as a text-based chat window accompanying the video conference which supports sharing of hyperlinks and/or sharing of media content, or via a picture-in-picture layout in which the additional content is immediately displayed, etc. Such sharing of content may also be referred to as 'posting', 'inserting', 'linking', etc.

Disadvantageously, the medical professional may need to be well prepared for sharing the additional content, or otherwise may lose time searching for the additional content during the communication session. In addition, the steps involved in sharing the content may take effort and distract the medical professional from communicating with the patient. It will be appreciated that same or similar problems may also occur in other fields besides the medical field.

There may thus be a need to facilitate sharing additional content which may be relevant in the communication session between two or more users.

It is known to provide computer-based assistance in a conversation. Depending on the context, the software entity providing such computer-based assistance may be referred to as a chatbot, virtual assistant, interactive agent, artificial conversational entity, etc., but is in the following simply referred to as 'chatbot' while noting that the computer-based assistance is not limited to text-based 'chats' but may rather apply to all kinds of communication sessions and modalities.

For example, U.S. Pat. No. 9,761,222B1 describes an intelligent conversational messaging system that is said to be able to take into account the context and content of the communication and provide assistance to one or more users, for example, within the field of customer service. The system receives through a conversation bridge one or more words communicated from a user, maps the one or more words to a repository of predefined conversation types, calculates one or more probabilities that the conversation is associated with one or more predefined conversation types, and displays a list of suggested conversation types on a digital display screen. A user, such as a customer service representative, may select a conversation type which causes an expert agent to be activated in the conversation which will then communicate with the user via the conversation bridge.

SUMMARY OF THE INVENTION

A disadvantage of known mechanisms to invoke chatbots, such as the intelligent conversational messaging system of U.S. Pat. No. 9,761,222B1, is that they may be insufficiently able to determine when to invoke the chatbot in a conversation between two human users, i.e., at which point during the conversation. For example, in the system of U.S. Pat. No. 9,761,222B1, a user has to manually initiate the expert agent by selecting a conversation type, or the system may automatically initiate the expert agent at 'any time' but without any other considerations regarding the timing.

It would be desirable for a chatbot to augment the conversation between two or more human users, for example by sharing additional content in the communication session, when appropriate within the context of their conversation. Accordingly, it would be advantageous to obtain a system and computer-implemented method which determines when to invoke a chatbot in an online communication session involving at least two participants.

The following aspects of the invention may involve generating an interaction model by way of training on past conversation data between participants of past communication sessions and metadata which is indicative of a sharing of additional content by one of the participants in the past communication session to augment the past verbal conversation. More specifically, the interaction model is trained to determine so-termed interaction points in the past conversation data which are predictive of a subsequent sharing of additional content by one of the participants. Having generated the interaction model, the interaction model may be applied to an online communication session to detect such interaction points in a real-time or near real-time conversation between users and to invoke a chatbot to participate in the communication session in response to a detection.

In accordance with a first aspect of the invention, a system is provided for determining when to invoke a chatbot in an online communication session involving at least two participants. The system comprises:
 an interface for obtaining, in real-time or near real-time, conversation data representing a verbal conversation between the participants in the online communication session;
 a processor subsystem configured to:
 access an interaction model which is trained on:
 past conversation data comprising text-based representations of past verbal conversations of participants of past communication sessions;
 metadata associated with the past conversation data and indicative of a sharing of additional content by one of the participants in the past communication session to augment the past verbal conversation;
 wherein the interaction model is trained to determine interaction points in the past conversation data, each interaction point representing a point in verbal conversation which is predictive of a subsequent sharing of additional content by one of the participants; and
 in real-time or near real-time:
 obtain a text-based representation of the verbal conversation between the participants from the conversation data;
 apply the interaction model to the text-based representation of the verbal conversation to detect an interaction point;
 in response to the detection of the interaction point, invoke the chatbot to participate in the online communication session by sharing additional content in the conversation between the participants.

In accordance with a further aspect of the invention, a computer-implemented method is provided for determining when to invoke a chatbot in an online communication session involving at least two participants. The method comprises:
 accessing an interaction model which is trained on:
 past conversation data comprising text-based representations of past verbal conversations of participants of past communication sessions;
 metadata associated with the past conversation data and indicative of a sharing of additional content by one of the participants in the past communication session to augment the past verbal conversation;
 wherein the interaction model is trained to determine interaction points in the past conversation data, each interaction point representing a point in verbal conversation which is predictive of a subsequent sharing of additional content by one of the participants; and
 in real-time or near real-time:
 obtaining a text-based representation of a verbal conversation between the participants in the online communication session;
 applying the interaction model to the text-based representation of the verbal conversation to detect an interaction point; and
 in response to the detection of the interaction point, invoking the chatbot to participate in the online communication session by sharing additional content in the conversation between the participants.

In accordance with a further aspect of the invention, a system is provided which is configured to train an interaction model for use in determining when to invoke a chatbot in an online communication session involving at least two participants. The system comprises:
 an interface for accessing:
 conversation data comprising text-based representations of past verbal conversations of participants of past communication sessions; and
 metadata associated with the conversation data and indicative of a sharing of additional content by one of the participants in the past communication session to augment the past verbal conversation;
 a processor subsystem configured to train the interaction model using the conversation data and the metadata as training data to determine interaction points in the conversation data, each interaction point representing a point in verbal conversation which is predictive of a subsequent sharing of additional content by one of the participants.

In accordance with a further aspect of the invention, a computer-implemented method is provided to train an interaction model for use in determining when to invoke a chatbot in an online communication session involving at least two participants. The method comprises:
 accessing conversation data comprising text-based representations of past verbal conversations of participants of past communication sessions;
 accessing metadata associated with the conversation data and indicative of a sharing of additional content by one of the participants in the past communication session to augment the past verbal conversation; and
 training the interaction model using the conversation data and the metadata as training data to determine interaction points in the conversation data, each interaction point representing a point in verbal conversation which is predictive of a subsequent sharing of additional content by one of the participants.

In accordance with a further aspect of the invention, a computer-readable medium is provided, the computer-readable medium comprising transitory or non-transitory data representing instructions arranged to cause a processor system to perform any of the computer-implemented methods.

The above measures involve generating an interaction model which is trained on text-based representations of conversations between human participants of past communication sessions, as well as on metadata which is indicative of a sharing of additional content by one of the participants in the past communication session to augment the past verbal conversation. For example, the metadata may indicate at which point in the conversation which type of additional content is shared by one of the participants. The metadata may be auxiliary data separate from the conversation data. In other words, the metadata may be non-conversational data of the communication session. For example, such metadata may be obtained in the form of logging information from a communication session backend which indicates when and what type of content a participant shares in the communication session.

The interaction model is then trained to determine so-termed interaction points in the past conversation data which are predictive of the intention of one of the participants to share additional content. Essentially, the interaction points represent points in the conversation, e.g., as represented by timestamps or conversation line numbers or other identifiers of conversation segments, which are expected to be followed by a sharing of additional content by one of the participants based on the training on the past conversation data and the associated metadata.

Having generated the interaction model, the interaction model may be applied to an online communication session to detect interaction points in a real-time or near real-time conversation between users. For that purpose, a text-based representation of the verbal conversation between the participant may be obtained, e.g., directly from a text-based chat, by transcribing a voice conversation using speech recognition techniques, etc. The interaction model is applied to the text-based representation, and a chatbot may be invoked to participate in the communication session in response to a detection of an interaction point in the text-based representation. Such invocation of the chatbot may then result in the chatbot sharing additional content in the conversation between the participants.

The above measures have the effect that the chatbot is invoked at specific points in the conversations, namely those points which, based on the training data of the interaction model, are expected to be otherwise followed by a sharing of additional content by one of the participants. To avoid the medical professional or similar user having to share the additional content themselves, the chatbot is invoked to assist the medical professional in the conversation by essentially taking over the task of sharing the additional content.

It is thus not needed for the medical professional or similar user to share the additional content themselves. Compared to known mechanisms to invoke chatbots, it is not needed for a user to be explicitly involved in the invocation. In particular, the invocation is timed such that the sharing of the additional content is appropriate in the conversation, namely at an interaction point in the conversation which is expected to be otherwise followed by a sharing such additional content.

Optionally, the processor subsystem is configured to apply the interaction model to individual segments of the text-based representation of the verbal conversation by, for a respective segment:
  extracting a feature vector from the text-based content of the respective segment; and
  using the feature vector as input to the interaction model to determine whether the respective segment represents an interaction point.

The presence of an invocation point may be specifically determined for segments of the text-based representation of the verbal conversation, for example for parts of the conversation representing alternating lines from each participant (henceforth also simply referred to as 'conversation lines'). For each of these segments, the presence of an invocation point may be determined on the basis of the textual content of the segment. More specifically, a feature vector may be extracted from the textual content and used as input to the interaction model. Thereby, the interaction model may determine whether the respective segment represents an interaction point. In accordance with this optional aspect, respective segments of the conversation may, on the basis of their content, be considered to represent interaction points in the conversation or not.

It will be understood by the skilled reader that a specific way of applying the interaction model may require the interaction model to have been trained in a corresponding manner, for example on the basis of a feature vector extracted from the text-based content of respective segments of past conversations. In general, such training is well within reach of the skilled person on the basis of the description of a specific way of applying of the interaction model. Parts of the description which relate to such ways of applying the interaction model thereby provide support for the corresponding training of the interaction model, mutatis mutandis, without being explicitly described.

Optionally, the processor subsystem is configured to extract the feature vector from the text-based content of the respective segment by extracting word-level features from the text-based content of the respective segment and generating the feature vector based on the word-level features. Various types of word-level features may be predictive of a user's intention to share of additional content. For example, medical keywords and/or word-level references to a type or semantic content of the additional keyword have been found to be highly indicative thereof. A specific example may be the conversation line "Let me see if I can find an illustration showing the correct way to apply the bandage to your knee", which may be indicative of a need to share an illustration ('type of additional content') of how to apply a bandage ('semantic content of the additional content, medical keyword') to the knee (Medical keyword).

Optionally, the processor subsystem is configured to extract the word-level features by detecting, in the text-based content of the respective segment, at least one of the group of:
  one or more keywords from a medical dictionary or ontology; and
  one or more word-level references to a type or a sematic content of the additional content.

Optionally, the processor subsystem is configured to provide the feature vector to the chatbot when invoking the chatbot to enable the chatbot to identify the additional content which is to be shared in the conversation on the basis of the feature vector. The feature vector may allow the chatbot to determine which additional content is to be shared in the conversation. As such, the feature vector may be provided to the chatbot, e.g., via an application programming interface (API) or in any other manner. In this respect, it is noted that it is not needed for the feature vector to be provided to the chatbot. Rather, alternative embodiments are conceived in which the chatbot determines which additional content is to be shared in the conversation using different techniques, for example by separately analyzing segments of the conversation.

Optionally, the metadata is non-conversational metadata, such as logging information of sharing actions by participants of the past communication sessions. Here, the term 'non-conversational' refers to the data being additional data next to the conversation data providing the text-based representation of the conversation of the participants. For example, the metadata may contain an automatic log of sharing actions of participants, e.g., in the form of "at timestamp X participant Y shared content Z" or similar forms. Another example is that the metadata may contain manual annotations of such sharing actions.

Optionally, the conversation data comprises audio data representing an audio recording of an oral conversation between the participants in the online communication session, and wherein the processor subsystem is configured to obtain the text-based representation of the verbal conversation between the participants by applying a speech recognition technique to the audio data. The audio data may thus be transcribed by the system in (near) real-time.

Optionally, the additional content comprises at least one of the group of:
  a media file, such as an image, video or audio file;
  a website or part thereof;
  an electronic health record or part thereof;
  a data representation of a medical prescription; and
  a data representation of a calendar entry.

Various types of additional content may be shared in the online communication session so as to augment the conversation, and the interaction model may be trained to detect interaction points which are predictive of the sharing of such types of additional content.

Optionally, a server or a distributed system of servers may be provided comprising the system for determining when to invoke a chatbot in an online communication session. For example, the server or the distributed system of servers may be configured to host or coordinate the online communication session. In another example, the server or the distributed system of servers may be configured to establish the chatbot. Effectively, the functionality of the aforementioned system may be implemented by the chatbot itself.

It will be appreciated by those skilled in the art that two or more of the above-mentioned embodiments, implementations, and/or optional aspects of the invention may be combined in any way deemed useful.

Modifications and variations of any computer-implemented method and/or any computer program product, which correspond to the described modifications and variations of a corresponding system, can be carried out by a person skilled in the art on the basis of the present description.

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the figures, elements which correspond to elements already described may have the same reference numerals.

LIST OF ABBREVIATIONS

API application programming interface
A/V audio/video
NLP natural language processing

LIST OF REFERENCE NUMBERS

The following list of reference numbers is provided for facilitating the interpretation of the drawings and shall not be construed as limiting the claims.

100 training set of conversation data and metadata
110 medical professionals
120 patients
130 interaction analysis module
140 context analysis module
150 natural language processing pre-processing module
155 machine learning-based interaction modeling module
160 interaction model
170 chatbot
200 conversation segments (lines)
210 interaction point
220 tokenizer
230 part-of-speech tagger
240 medical dictionary or ontology
250 medical entity recognizer
260 content type dictionary
270 content type detector
280 feature vector generation module
300 messaging backend
302 backend data communication
320 content backend
340 chatbot extension
342 chatbot Q&A flow
360 algorithm framework
362 real-time communication API
380 chatbot backend
382 chatbot API
400 'creates'
410 'joins'
420 'calls'
430 online communication session
440 first user
442 second user
450 communication data
460 chatbot user
500 system
510 interface
520 processor subsystem
530 storage
600 method for training interaction model
610 accessing conversation data
620 accessing metadata
630 training interaction model
700 method for determining invocation of chatbot
710 accessing interaction model
720 obtaining conversation data
730 obtaining text-based representation of conversation
740 applying interaction model
750 invoking chatbot
800 computer-readable medium
810 non-transitory data

DETAILED DESCRIPTION OF EMBODIMENTS

The following describes the generating and subsequent use of an interaction model by way of training on past conversation data between participants of past communication sessions and metadata which is indicative of a sharing of additional content by one of the participants in the past communication session to augment the past verbal conversation. More specifically, the interaction model may be trained to determine so-termed interaction points in the past conversation data which are predictive of a subsequent sharing of additional content by one of the participants. Having generated the interaction model, the interaction model may be applied to an online communication session to detect such interaction points in a real-time or near real-time conversation between users and to invoke a chatbot to participate in the communication session in response to a detection.

An example of a verbal conversation between a medical professional, such as a clinician, and a patient may look as follows. This conversation may take place via a text-based chat, or may represent a transcript of a voice-based conversation, etc. Time stamps (t1-t11) identify conversation lines in time.

| Conversation 1: | | |
|---|---|---|
| t1 | Clinician | Hello John, how are you? |
| t2 | Patient | I am fine doctor. |
| t3 | Clinician | I see that your blood pressure readings are showing some variations compared to last week. Are you taking your blood pressure medication? |
| t4 | Patient | Yes, I am taking it regularly. |
| t5 | Clinician | Are you using the blood pressure monitor correctly by placing the cuff in the correct position? |
| t6 | Patient | I think I'm using it properly. |
| t7 | Clinician | Just to make sure you get the cuff position right, let me search for a picture of how it is done. |
| t8 | Patient | Ok doctor. |
| t9 | Clinician | There it is. Please have a look. |
| t10 | Patient | Yes, I can see it. I will try to maintain the 2 inches distance from the elbow joint as shown in the picture. |
| t11 | Clinician | Ok, please continue with your medication and let's review in a week's time. |

Metadata associated with the above text-based representation of the conversation may indicate that a picture is shared at timestamp t9. As will be elucidated further onwards, the conversation line at timestamp t7 may represent an interaction point in the conversation which is predictive of the intention of the clinician to share the picture, e.g., by the clinician referring to 'let me search for a picture'. The interaction model may be trained to detect such and similar types of interaction points in text-based representation of conversations, for example using the above conversation and associated metadata as part of its training data.

Another example of a conversation is the following:

| Conversation 2: | | |
|---|---|---|
| t1 | Clinician | Hello Jane, how are you? |
| t2 | Patient | I am generally fine but I'm experiencing a burning pain in the chest that usually occurs after eating. |
| t3 | Clinician | Ok, does it worsen when you lie down? Have you observed any foods that triggers such pain? |
| t4 | Patient | Yes, whenever I have mild spicy food or coffee I get this pain. |
| t5 | Clinician | You might be suffering from acid reflux and need to be put on antacids for some time. Let me see if I can show you a small animation of what happens during acid reflux to make it clear. |
| t6 | Patient | Ok doctor. |
| t7 | Clinician | Here it goes. Can you see it? |
| t8 | Patient | Yes, I can see the animation. |
| t9 | Clinician | You might also need to raise your bed on your head side by about 6 inches. |
| t10 | Patient | Ok doctor. Should I use pillows? |
| t11 | Clinician | No, you need to raise the entire cot on your head side. Let me search for a picture. Ah here it is. Can you see it? |
| t12 | Patient | Got it. I will do this. |
| t13 | Clinician | Ok, I will prescribe medication for your acid reflux and you should feel better. Let's have another review in a week and don't hesitate to reach out to me if you have any discomfort or doubts. |
| t14 | Patient | Thank you doctor. |

Metadata associated with the above text-based representation of the second conversation may indicate that a video is shared at timestamp t7 and that a picture is shared at timestamp t12. The conversation lines at timestamps t5 and t11 may represent the respective interaction points which are predictive of the intention of the clinician to share the respective additional content.

Figure 1:
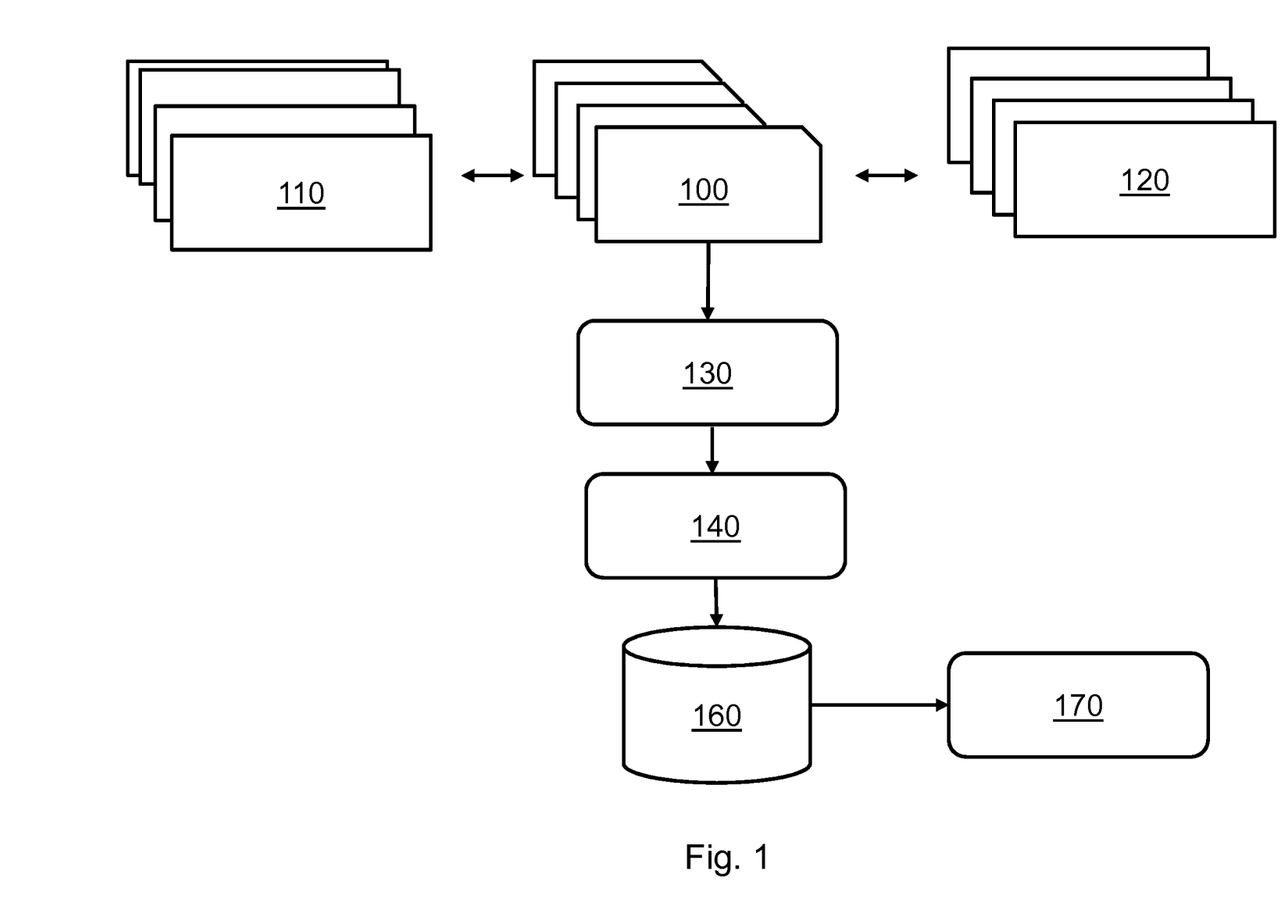
FIG. 1 shows functional modules of a system which uses machine learning to generate an interaction model for use in determining when to invoke a chatbot in an online communication session.
Figure 2:
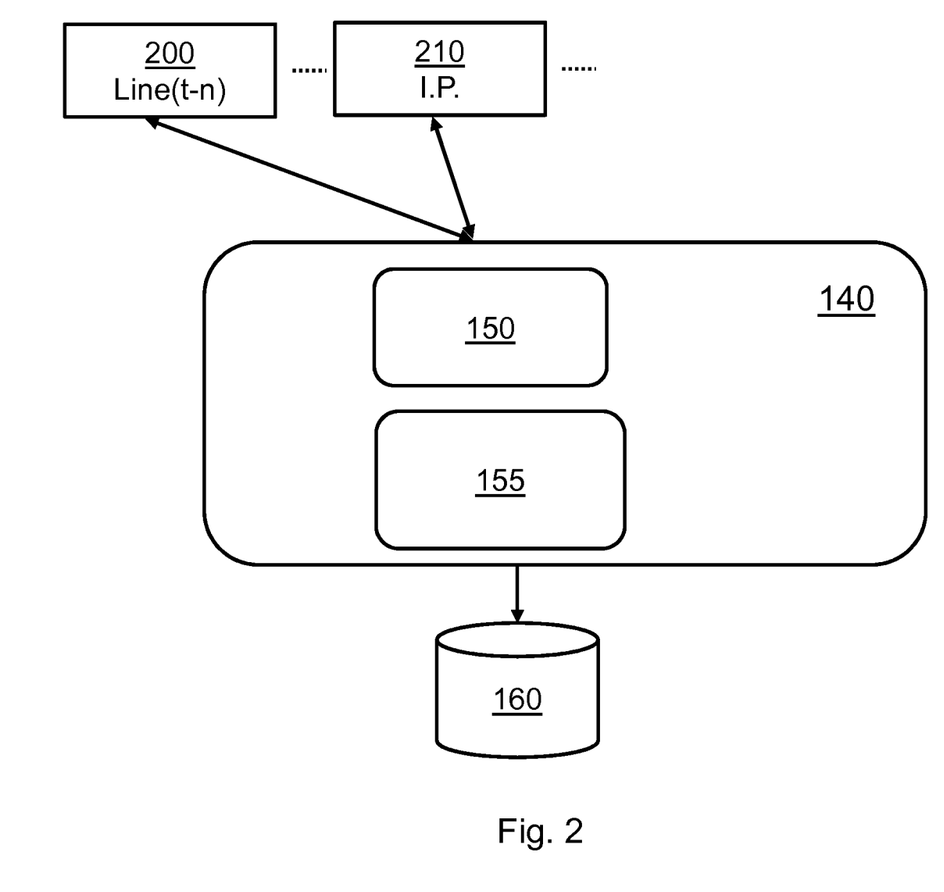
FIG. 2 shows a detailed view of a context analysis module.
Figure 3:
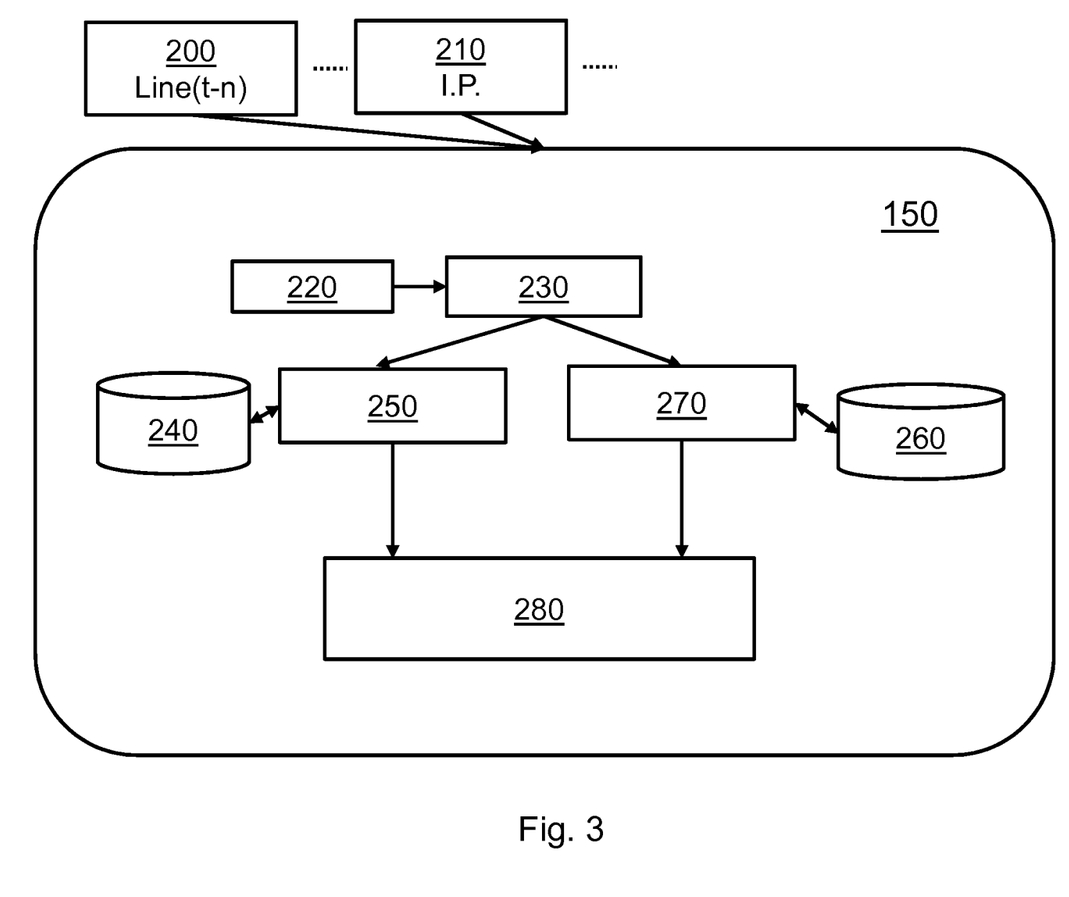
FIG. 3 shows a detailed view of a natural language processing pre-processing module of the context analysis module.
Figure 4:
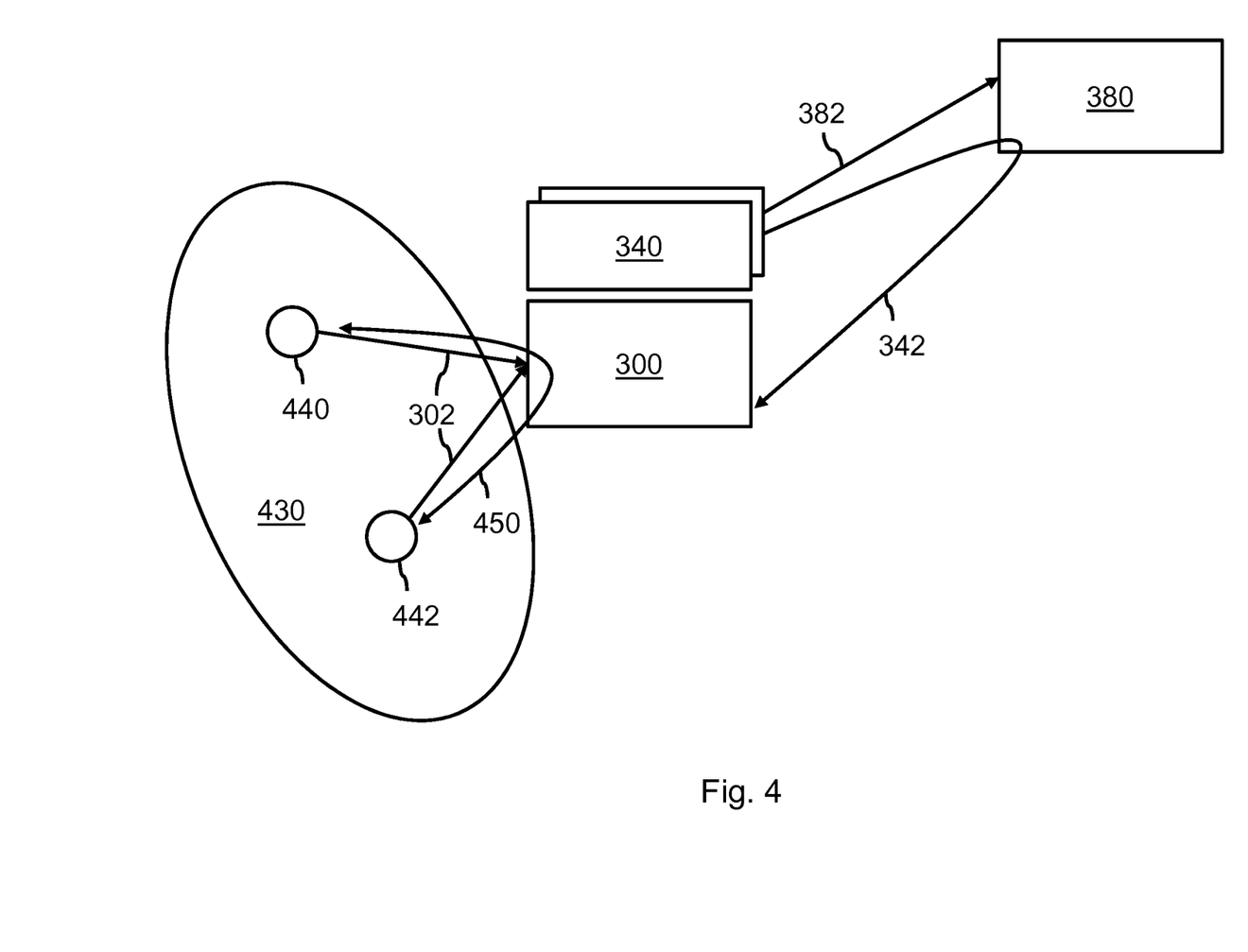
FIG. 4 shows an embodiment of a system for determining when to invoke a chatbot in an online communication session, in which the system is implemented as an extension to a real-time communication messaging backend.
Figure 5:
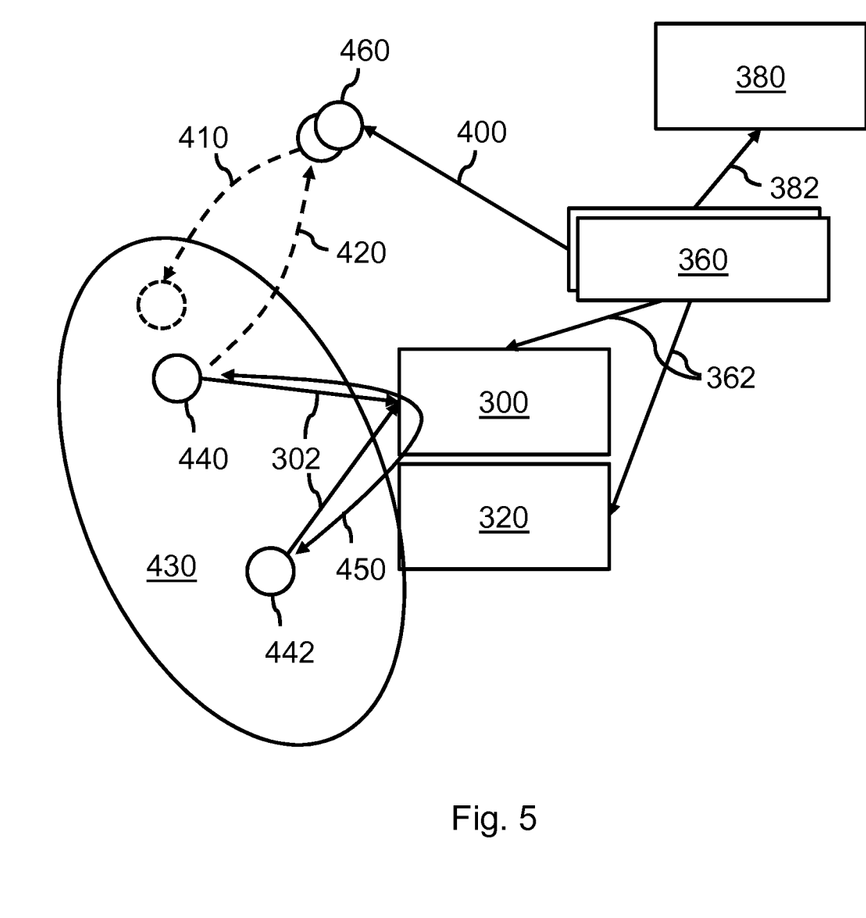
FIG. 5 shows another embodiment of a system for determining when to invoke a chatbot in an online communication session, which uses an algorithm framework which is capable of creating a headless conference participant.

The following describes, with reference to FIGS. 1-3, a system for generating the interaction model, and, with reference to FIGS. 4 and 5, a system for using the interaction model during a (near) real-time communication session.

FIG. 1 shows functional modules 130, 140 of a system which uses machine learning to generate an interaction model for use in determining when to invoke a chatbot 170 in an online communication session. It will be appreciated that these and subsequent modules may be implemented by a processor system, for example as software, hardware, or a combination thereof, as also elucidated with reference to FIG. 6 and others. In such an implementation, the partitioning of the functionality into the described modules may be maintained, for example as corresponding software modules, but also a different or no partitioning may be used.

With continued reference to FIG. 1, a training set 100 may be obtained which may comprise conversation data and associated metadata (neither of which is explicitly shown in FIG. 1). The conversation data may contain text-based representations of past verbal conversations of participants during past communication sessions, for example, between medical professionals 110 and patients 120, whereas the metadata may be indicative of a sharing of additional content by one of the participants in the past communication session to augment the past verbal conversation. Such a training set 100 may, for example, be obtained from chatlogs or other logging information of past communication sessions.

The training set 100 may then be analyzed by an interaction analysis module 130 to identify interaction points to be used as input to a subsequent training. For example, a conversation segment containing the text "Let me explain with a picture what migraine headache is" which is followed by a participant sharing a picture, may be identified as an interaction point. Such interaction points may be extracted for all conversations in the training set, for example in the manner described below. It is noted that alternatively, the system may use a training set in which the interaction points have been manually or in any other way identified.

It is noted that if the conversation data does not comprise a text-based representation of the verbal conversation, but rather for example audio or audio-video (AV) content, the text-based representation may first be obtained by the system, for example using a speech recognition technique to obtain a transcription.

For example, the following steps may be performed by the system:

1) If not already the case, the conversation data may be transcribed to text, e.g., using a speech recognition technique.

2) If not already the case, the conversation data and associated meta data may be time stamped or in any other way marked or segmented in time.

3) Using the metadata, instances of a participant sharing additional content may be identified. For example, in conversation 1, this may include the picture being shared at timestamp t9, while in conversation 2, this may include the video being shared at timestamp t7 and the picture being shared at timestamp t12.

4) Using the text-based representation of the conversation, interaction points may be identified which may be predictive of the sharing of this additional content. This may for example be performed by searching for word-level references for a type of additional content, e.g., a 'picture', 'video', 'illustration', etc., but also to word-level references to sharing, e.g., 'let me show you', 'I'll try to share', etc. In some embodiments, the searching may be specific to the type or the semantic content of the additional content which was found to have been shared on the basis of the metadata. In some embodiments, this search may be time-limited, e.g., within a range before the sharing of the additional content as identified from the metadata.

For example, with continued reference to conversations 1 and 2, in conversation 1, an interaction point may be detected at timestamp t7, whereas in conversation 2, interaction points may be detected at timestamps t5 and t11.

The context analysis module 140 may then analyze the interaction points identified by the interaction analysis module 130. FIG. 2 shows a detailed view of the context analysis module 140, which may use (parts of) the text-based representation 200 of the conversations of the training set and the identified interaction points 210 as input and generate an interaction model 160 as output.

For example, parts of the conversations before the identified interaction points, e.g., a range of conversation lines 200 between timestamp t at which an interaction point is detected and timestamp t-n before said time, may be used along with the interaction points 210 as input to a Natural Language Processing (NLP)-based pre-processing module 150 to extract word-level feature such as a type of additional content, e.g., a media type such as a picture/video/audio, which may then be used as input to a machine learning-based interaction modeling module 155.

FIG. 3 shows a detailed view of the NLP-based pre-processing module 150 of the context analysis module 140. Briefly speaking, the NLP-based pre-processing module 150 contains a feature extraction module 280 which may generate feature vectors for two classes, namely for conversation lines 200 (or in general for conversation segments) which have been identified to represent interaction points 210, and for those not identified to represent interaction points.

For that purpose, the NLP-based preprocessing module may use a tokenizer 220 and a part-of-speech tagger 230 to generate word level features, e.g., in a manner as known per se from NLP, for example using the term frequency/inverse document frequency (tf-idf) technique and using known Part-Of-Speech (POS) taggers such as the Stanford POS tagger which identifies the words as nouns, adverbs, adjectives, etc. A medical entity recognizer 250 may receive the word level features as input and identify medical keywords using a medical dictionary or ontology 240. A content type detector 270 may receive the word level features as input and detect content types based on a category type dictionary 260.

The feature vector generation module 280 may then combine:
- the extracted word level features,
- detected medical keywords, and
- detected content types, to create a feature vector for each interaction point. Feature vectors may also be created for conversation lines which do not represent interaction points.

For example, with continued reference to conversation 1, the conversation lines from t5 to t9 may be fed into the NLP-based pre-processing module 150 to extract features such as: Content type=picture
Keywords=blood pressure monitor, blood pressure readings, cuff position, cuff position picture The feature vector generation module 280 may then generate a feature vector f1 of the form of f1=w[1], ..., w[n], m[1], ..., m[n], k[1], ... k[n], IP[Yes/No], where:
w—selected words
m—content (e.g. media) type
k—keywords
IP—class of interaction point or not interaction point Here, the interaction point may be at t7, the confirmation of the interaction point (by way of the sharing of the additional content) may be at t9, and t4-t9 may represent a temporal window from which a context of the interaction point may be determined. The size of this window may vary depending on application and may be expressed as a number of lines, but also any other way. For example, the temporal window may be selected to be 2 or 3 lines before the interaction point.

Similarly, for the conversation lines at t1, t2, t3, t4 which are not considered to potentially represent interaction points by being outside of the aforementioned temporal window t5-t9 and thereby do not belong to the class 'interaction point' ('IP[Yes]'), a feature vector f2 may be generated.

With continued reference to FIG. 2, the feature vectors may be used as input to a machine learning-based interaction modelling module 155 which may use the feature vectors (f1, f2, ..., fn) as an input vector and may use the input vector to train a two-class classifier-based machine learning algorithm, for example a Support Vector Machine/Decision Tree/Neural Network-based algorithm, to classify these feature vectors into either an interaction point or a non-interaction point. The interaction model, which may effectively represent a trained classifier, may be tuned to improve its accuracy, for example using hyper parameter tuning algorithms such as grid search or genetic algorithms. The feature extraction may also be improved using reinforcement learning, e.g., to determine the temporal window for which features of an interaction point class are to be extracted. For example, the temporal window may encompass a select number of conversation lines. In general, the contents of the temporal window may be used for determining the interaction point's context.

With continued reference to FIG. 2, the output of the context analysis module 140 may be a trained interaction model 160 which may then be used by a chatbot 170 itself, or by another entity (system), to determine when the chatbot is to be invoked in an online communication session. The following may refer to such use of the interaction model 160 by the chatbot, but any descriptions relating to this use are to be understood as being equally applicable to the use by another entity (system).

Such use of the interaction model 160 is further described with reference to FIGS. 4 and 5 and others but may involve the chatbot 170 joining the conversation based on a detection of an interaction point in the conversation, with the chatbot then sharing additional content, such as video/audio/slides, to augment the conversation. During deployment, a database of shared additional content may be maintained for faster retrieval during future conversations. In general, the chatbot 170 may learn from conversation feedback, e.g., to better detect interaction points and/or to share more relevant additional content. The former may involve the chatbot or another entity retraining the interaction model 160 after deployment.

A result of the use of the interaction model 160 may be the following, commencing in the same manner as the previous conversation 1 while illustrating the course of the conversation when the chatbot is invoked at an interaction point:

| | | Conversation 1*: |
|---|---|---|
| t1 | Clinician | Hello John, how are you? |
| t2 | Patient | I am fine doctor. |
| t3 | Clinician | I see that your blood pressure readings are showing some variations compared to last week. Are you taking your blood pressure medication? |
| t4 | Patient | Yes, I am taking it regularly. |
| t5 | Clinician | Are you using the blood pressure monitor correctly by placing the cuff in the correct position? |
| t6 | Patient | I think I'm using it properly. |
| t7 | Clinician | Just to make sure you get the cuff position right, let me search for a picture of how it is done. |
| t8 | Chatbot | Hello doctor, do you want to show me an appropriate picture of the cuff position? |
| t9 | Clinician | Go ahead. |
| t10 | Chatbot | Is this picture fine, doctor? |
| t11 | Clinician | Yes, this is fine. Please have a look John. |
| t12 | Patient | Yes, I can see it. I will try to maintain the 2 inches distance from the elbow joint as shown in the picture. |
| t13 | Clinician | Ok, please continue with your medication and let's review in a week's time. |

In this conversation, it may be determined, using the interaction model, that the chatbot is to join the conversation at time t7 and share the additional content to which the clinician referred. Both the clinician and the patient may be made aware that the context aware chatbot is listening to their conversation and may join when appropriate to augment the conversation. In this way, the time and effort of the clinician for searching the appropriate content may be reduced and a better engagement with patient may be achieved. The shared additional content may be stored by the chatbot in a database for faster retrieval for future conversations. Such storing may be subject to the clinician providing positive feedback on the appropriateness of the additional content which is shared by the chatbot.

With further reference to the deployment of the interaction model, i.e., its use to determine when to invoke the chatbot during a communication session, it is noted that the communication session may be established via a communication platform, which is in the following, by way of example, a video-conferencing platform. However, this is not a limitation, in that the functionality of determining when to invoke the chatbot may be implemented with any suitable communication platform. In this respect, it is noted that the following embodiments refer to a server-based communication platform, in which the functionality of determining when to invoke the chatbot is implemented by a backend system of the chatbot. However, this is not a limitation, in that the communication platform may also be implemented by any other (backend) system or server, but also in a non-centralized manner, e.g., using peer-to-peer (P2P) technology. In the latter example, the chatbot may participate in the communication session as an ordinary user, while the functionality of determining when to invoke the chatbot may be implemented by the chatbot itself.

In general, an online communication session may involve:
1. A communication platform The communication platform, which may for example be a video conference platform, may be a real-time or near real-time communication platform which preferably provides a low latency connection between the different participants of the communication session, for example the clinician, patient and chatbot. After the communication session has started, the chatbot may be invited by a participant, e.g., the clinician, or may automatically join the communication session, e.g., as a third, 'headless' participant. From that moment, the chatbot may receive all data streams of the communication session, e.g., audio, video or data streams.

2. A chatbot

The chatbot may use the interaction model trained on previous conversations to determine in which context it should join the conversation by sharing additional content. The chatbot may thus be considered 'context-aware'.

FIGS. 4 and 5 represent alternatives for implementing a system for determining when to invoke a chatbot in an online communication session. Both are non-limiting examples, in that various other implementations are also feasible.

FIG. 4 shows a first embodiment of a system for determining when to invoke a chatbot in an online communication session, in which the system is implemented as an extension to a real-time communication messaging backend.

More specifically, FIG. 4 shows a visualization of an online communication session 430 which has a first user 440 and a second user 442 as participants. Further shown is a generalized messaging backend 300 which is an example of a messaging backend of a communication platform and which may be capable of hosting chat conferences. Chat-bot extension 340 may extend the messaging backend 300 by tapping into messages of, for example, all conferences and all users, and may then use chat-bot API 382 to pass these messages to the chat-bot backend 380. The same API 382 may also be used by the chat-bot backend 380 to pass the responses to the chat-bot extension 340 and the chat-bot extension may push the response into a specific conference, or maybe to a specific person in the conference, e.g., a clinician. Q&A flow 342 may represent all the messages of all the conferences and all the responses that are passed between the chat-bot backend 380 and the chat-bot extension 340 using chat-bot API 382. In other words, the chat-bot API may be a two-way API, e.g., a request-response API.

FIG. 4 shows a relatively simple way to extend a communication messaging backend to support and interact with the described chat-bot.

FIG. 5 shows a second embodiment of a system for determining when to invoke a chatbot in an online communication session, which uses an algorithm framework 360 which is capable of creating a headless conference participant 460 representing the chatbot, and once this participant joins the conference, of accessing all the streams (chat, audio, video, data) of the conference. To be able to access all the streams, the headless participant 460 may first need to join 410 the conference 430. This may be done automatically by the algorithm framework 360 when the conference is created. If not, then any user of the conference, e.g., a clinician, may call 420 the chatbot at the moment when it is needed. From that moment onwards, the chatbot becomes participant 460 in the conference 430, and all the conference messages may be transferred to the chat-bot backend 320 in a same or similar manner as already described with FIG. 4. Once the interaction point is detected in the course of the conversation, the chatbot can choose to offer not only messages and images as information to the participants but also audio, video or other data.

Figure 6:
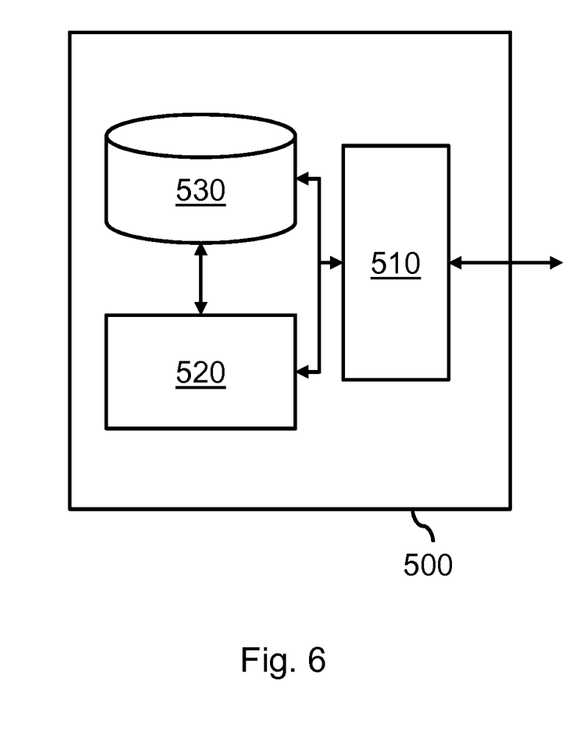
FIG. 6 shows an exemplary processor system.

FIG. 6 shows an exemplary processor system 500 which may implement a system for determining when to invoke a chatbot in an online communication session involving at least two participants, or a system configured to train an interaction model for use in determining when to invoke a chatbot in an online communication session involving at least two participants, or both. FIG. 6 shows the system 500 to comprise an interface 510 for communicating with (other) entities, such as other network nodes in a network. The interface 510 may be an external interface and take any suitable form, including but not limited to a network interface such as a wired network interface based on Ethernet or optical fiber or a wireless network interface. In some embodiments, the interface 510 may be an internal interface, e.g., to another part of the system 500.

FIG. 6 further shows the system 500 comprising a storage 530, such as a hard disk, a solid-state drive, or an array thereof, which may be used by the system 500 for storing data, such as a trained interaction model.

The system 500 may further comprise a processor subsystem 520 which may be configured, e.g., by hardware design or software, to perform the operations described with reference to FIG. 1-6 in as far as pertaining to the training of the interaction model and/or the use of the trained interaction model. For example, the processor subsystem 520 may be embodied by a single Central Processing Unit (CPU), but also by a combination or system of such CPUs and/or other types of processing units. In general, the system 500 may be embodied by a (single) device or apparatus but also by a distributed system of such devices or apparatuses. The aforementioned device or apparatus may comprise one or more (micro)processors which execute appropriate software. Software implementing the functionality of the function(s) may have been downloaded and/or stored in a corresponding memory or memories, e.g., in volatile memory such as RAM or in non-volatile memory such as Flash. Alternatively, the function(s) may be implemented in the device or apparatus in the form of programmable logic, e.g., as a Field-Programmable Gate Array (FPGA). In general, each function may be implemented as a circuit.

Figure 7:
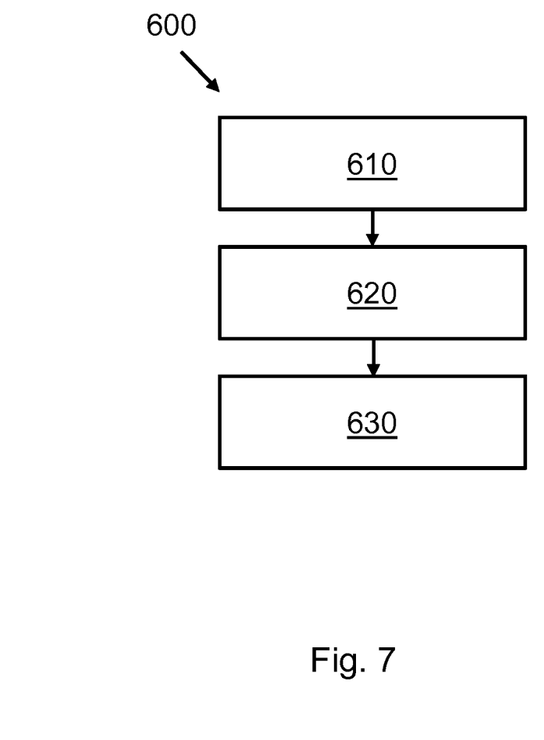
FIG. 7 shows a block-diagram of a computer-implemented method of training an interaction model for use in determining when to invoke a chatbot.

FIG. 7 shows a block-diagram of computer-implemented method 600 of training an interaction model for use in determining when to invoke a chatbot. The method 600 may comprise, in an operation titled "ACCESSING CONVERSATION DATA", accessing 610 conversation data comprising text-based representations of past verbal conversations of participants of past communication sessions. The method 600 may further comprise, in an operation titled "ACCESSING METADATA", accessing 620 metadata associated with the conversation data and indicative of a sharing of additional content by one of the participants in the past communication session to augment the past verbal conversation. The method 600 may further comprise, in an operation titled "TRAINING INTERACTION MODEL", training 630 the interaction model using the conversation data and the metadata as training data to determine interaction points in the conversation data, each interaction point representing a point in verbal conversation which is predictive of a subsequent sharing of additional content by one of the participants.

Figure 8:
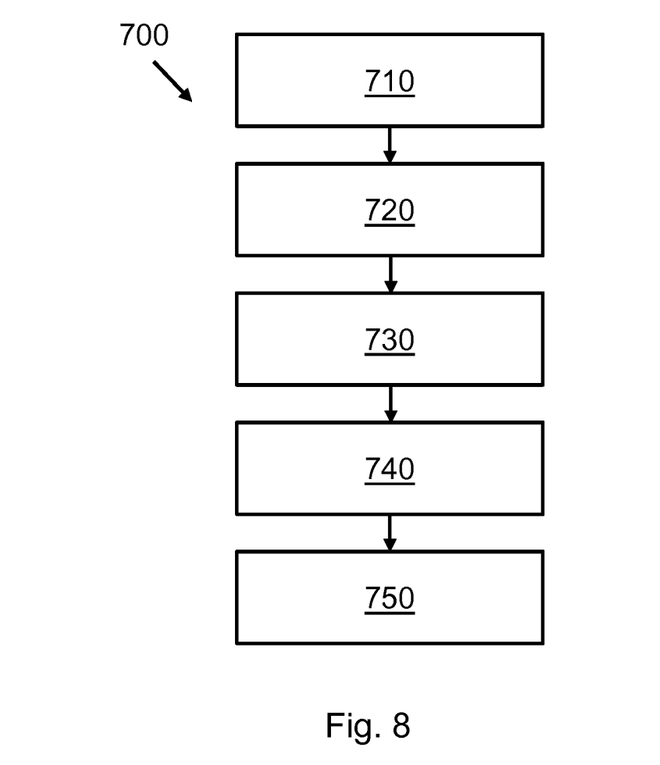
FIG. 8 shows a block-diagram of a computer-implemented method of using the interaction model to determine when to invoke a chatbot.

FIG. 8 shows a block-diagram of a computer-implemented method 700 of using the interaction model to determine when to invoke a chatbot. The method 700 may comprise, in an operation titled "ACCESSING INTERACTION MODEL", accessing 710 an interaction model as generated as described elsewhere in this specification. The following operations may be performed in real-time or near real-time: the method 700 may comprise, in an operation titled "OBTAINING CONVERSATION DATA", obtaining 720 conversation data representing a verbal conversation between the participants in the online communication session, in an operation titled "OBTAINING TEXT-BASED REPRESENTATION OF CONVERSATION", obtaining 730 a text-based representation of the verbal conversation between the participants from the conversation data, in an operation titled "APPLYING INTERACTION MODEL", applying 740 the interaction model to the text-based representation of the verbal conversation to detect an interaction point, and in an operation titled "INVOKING CHATBOT", in response to the detection of the interaction point, invoking 750 the chatbot to participate in the online communication session by sharing additional content in the conversation between the participants.

It is noted that, in some embodiments, the operations 720 and 730 may be (part of) a same operation if the conversation data contains the text-based representation of the conversation. In other embodiments, the conversation data may contain another representation of the conversation, e.g., an audio recording, and the obtaining of the text-based representation may comprise a processing of the conversation data, e.g., by means of a speech recognition technique.

It will be appreciated that, in general, the operations of method 600 of FIG. 7 and/or method 700 of FIG. 8 may be performed in any suitable order, e.g., consecutively, simultaneously, or a combination thereof, subject to, where applicable, a particular order being necessitated, e.g., by input/output relations.

Figure 9:
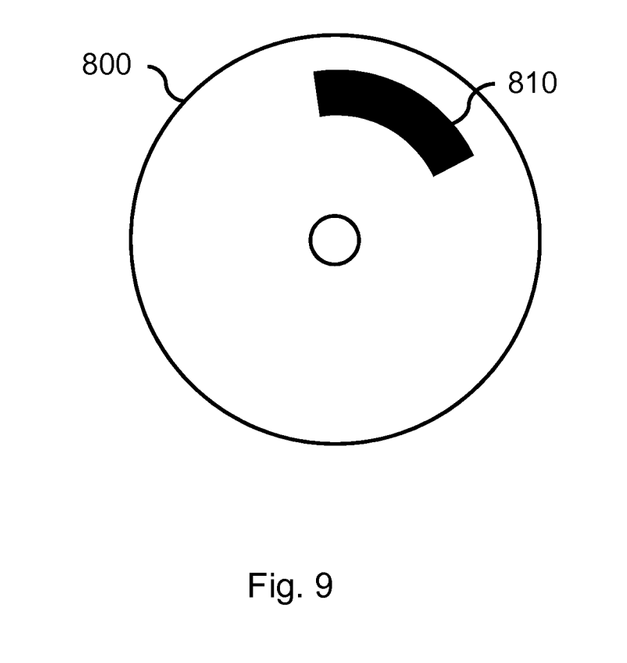
FIG. 9 shows a computer-readable medium comprising data.

The method(s) may be implemented on a computer as a computer implemented method, as dedicated hardware, or as a combination of both. As also illustrated in FIG. 9, instructions for the computer, e.g., executable code, may be stored on a computer readable medium 800, e.g., in the form of a series 810 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 9 shows an optical disc 800.

Alternatively, the computer readable medium 800 may comprise transitory or non-transitory data 810 representing an interaction model which is trained to determine interaction points in conversation data, the conversation data comprising text-based representations of past verbal conversations of participants of past communication sessions, each interaction point representing a point in verbal conversation which is predictive of a subsequent sharing of additional content by one of the participants in the past communication session to augment the past verbal conversation.

In accordance with an abstract of the present application, a chatbot may be invoked in an online communication session between two or more human users to share additional content in the communication session. To determine when to invoke the chatbot, e.g., at which point during their conversation, an interaction model may be trained on past conversation data between participants to determine so-termed interaction points in the past conversation data which are predictive of a subsequent sharing of additional content by one of the participants. Having generated the interaction model, the interaction model may be applied to an online communication session to detect such interaction points in a real-time or near real-time conversation between users and to invoke the chatbot to participate in the communication session in response to a detection.

Examples, embodiments or optional features, whether indicated as non-limiting or not, are not to be understood as limiting the invention as claimed.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. Expressions such as "at least one of" when preceding a list or group of elements represent a selection of all or of any subset of elements from the list or group. For example, the expression, "at least one of A, B, and C" should be understood as including only A, only B, only C, both A and B, both A and C, both B and C, or all of A, B, and C. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for determining when to invoke a chatbot in an online communication session involving at least two participants the system comprising:
   an interface for obtaining, in real-time or near real-time, conversation data representing a verbal conversation between the participants in the online communication session;
   a processor subsystem configured to:
   access an interaction model which is trained on:
      past conversation data comprising text-based representations of past verbal conversations of participants of past communication sessions; and
      metadata associated with the past conversation data and indicative of a sharing of additional content by one of the participants in the past communication session to augment the past verbal conversation, wherein the metadata is non-conversational metadata;
   wherein the interaction model is trained to determine interaction points in the past conversation data, each interaction point representing a point, corresponding to use of a word or phrase by one of the participants of the past communication sessions that suggests a desire by the one of the participants to further illustrate the word or phrase, in verbal conversation, which is predictive of a subsequent sharing of additional content by the one of the participants; and in real-time or near real-time:
   obtain a text-based representation of the verbal conversation between the participants from the conversation data;
   apply the interaction model to the text-based representation of the verbal conversation to detect an interaction point; and
   in response to the detection of the interaction point, invoke the chatbot to participate in the online communication session by sharing additional content in the conversation between the participants.

2. The system according to claim 1, wherein the processor subsystem is configured to apply the interaction model to individual segments of the text-based representation of the verbal conversation by, for a respective segment:
   extracting a feature vector from the text-based content of the respective segment; and
   using the feature vector as input to the interaction model to determine whether the respective segment represents an interaction point.

3. The system according to claim 2, wherein the processor subsystem is configured to extract the feature vector from the text-based content of the respective segment by extracting word-level features from the text-based content of the respective segment and generating the feature vector based on the word-level features.

4. The system according to claim 3, wherein the processor subsystem is configured to extract the word-level features by detecting, in the text-based content of the respective segment, at least one of the group of:
   one or more keywords from a medical dictionary or ontology; and
   one or more word-level references to a type or a sematic content of the additional content.

5. The system according to claim 2, wherein the processor subsystem is configured to provide the feature vector to the chatbot when invoking the chatbot to enable the chatbot to identify the additional content which is to be shared in the conversation on the basis of the feature vector.

6. The system according to claim 1, wherein the non-conversational metadata comprises logging information of sharing actions by participants of the past communication sessions.

7. The system according to claim 1, wherein the additional content comprises at least one of the group of:
   a media file, such as an image, video or audio file;
   a website or part thereof;
   an electronic health record or part thereof;
   a data representation of a medical prescription; and
   a data representation of a calendar entry.

8. A server or a distributed system of servers comprising the system according to claim 1.

9. The server or the distributed system of servers according to claim 8, wherein the server or servers are configured to establish the chatbot.

10. A computer-implemented method of determining when to invoke a chatbot in an online communication session involving at least two participants, the method comprising:
   accessing an interaction model which is trained on:
      past conversation data comprising text-based representations of past verbal conversations of participants of past communication sessions;
      metadata associated with the past conversation data and indicative of a sharing of additional content by one of the participants in the past communication session to augment the past verbal conversation, wherein the metadata is non-conversational metadata;
   wherein the interaction model is trained to determine interaction points in the past conversation data, each interaction point representing a point, corresponding to use of a word or phrase by one of the participants of the past communication sessions that suggests a desire by the one of the participants to further illustrate the word or phrase, in verbal conversation, which is predictive of a subsequent sharing of additional content by the one of the participants; and in real-time or near real-time:
   obtaining a text-based representation of a verbal conversation between the participants in the online communication session;
   applying the interaction model to the text-based representation of the verbal conversation to detect an interaction point; and in response to the detection of the interaction point, invoking the chatbot to participate in the online communication session by sharing additional content in the conversation between the participants.

11. A computer-readable medium comprising transitory or non-transitory data representing instructions arranged to cause a processor system to perform the computer-implemented method according to claim 10.

12. A system configured to train an interaction model for use in determining when to invoke a chatbot in an online communication session involving at least two participants the system comprising:
　an interface for accessing:
　　conversation data comprising text-based representations of past verbal conversations of participants of past communication sessions; and
　　metadata associated with the conversation data and indicative of a sharing of additional content by one of the participants in the past communication session to augment the past verbal conversation, wherein the metadata is non-conversational metadata;
　a processor subsystem configured to train the interaction model using the conversation data and the metadata as training data to determine interaction points in the conversation data, each interaction point representing a point, corresponding to use of a word or phrase by one of the participants of the past communication sessions that suggests a desire by the one of the participants to further illustrate the word or phrase, in verbal conversation, which is predictive of a subsequent sharing of additional content by the one of the participants.

13. A computer-implemented method to train an interaction model for use in determining when to invoke a chatbot in an online communication session involving at least two participants, the method comprising:
　accessing conversation data comprising text-based representations of past verbal conversations of participants of past communication sessions;
　accessing metadata associated with the conversation data and indicative of a sharing of additional content by one of the participants in the past communication session to augment the past verbal conversation, wherein the metadata is non-conversational metadata; and
　training the interaction model using the conversation data and the metadata as training data to determine interaction points in the conversation data, each interaction point representing a point, corresponding to use of a word or phrase by one of the participants of the past communication sessions that suggests a desire by the one of the participants to further illustrate the word or phrase, in verbal conversation, which is predictive of a subsequent sharing of additional content by the one of the participants.

14. A computer-readable medium comprising transitory or non-transitory data representing instructions arranged to cause a processor system to perform the computer-implemented method according to claim 13.

\* \* \* \* \*